US009763800B2

(12) United States Patent
Finley et al.

(10) Patent No.: US 9,763,800 B2
(45) Date of Patent: Sep. 19, 2017

(54) IMPLANT CONFIGURED FOR HAMMERTOE AND SMALL BONE FIXATION

(71) Applicant: Biomet C.V., Gibraltar (GI)

(72) Inventors: Adam Finley, Winona Lake, IN (US); Jacy Hoeppner, Warsaw, IN (US); Kevin Stone, Winona Lake, IN (US)

(73) Assignee: Biomet C. V., Warsaw, IN (US)

( * ) Notice: Subject to any disclaimer, the term of this patent is extended or adjusted under 35 U.S.C. 154(b) by 9 days.

(21) Appl. No.: 14/661,250

(22) Filed: Mar. 18, 2015

(65) Prior Publication Data

US 2016/0270923 A1 Sep. 22, 2016

(51) Int. Cl.
*A61F 2/42* (2006.01)
*A61B 17/064* (2006.01)
*A61B 17/84* (2006.01)

(52) U.S. Cl.
CPC ........ *A61F 2/4225* (2013.01); *A61B 17/0642* (2013.01); *A61B 17/84* (2013.01);
(Continued)

(58) Field of Classification Search
CPC ............ A61F 2/4225; A61F 2002/3012; A61F 2002/30817; A61F 2/0063; A61B 17/0642; A61B 17/84
See application file for complete search history.

(56) References Cited

U.S. PATENT DOCUMENTS 5,015,248 A * 5/1991 Burstein ................ A61B 17/68
606/297
5,443,516 A * 8/1995 Albrektsson ............ A61F 2/384
606/70
(Continued)

FOREIGN PATENT DOCUMENTS

CN 103767781 A 5/2014
DE 102008010476 A1 8/2009
(Continued)

OTHER PUBLICATIONS

"International Application Serial No. PCT/US2016/023094, International Search Report mailed Nov. 3, 2016", 7 pgs.
(Continued)

*Primary Examiner* — Bruce E Snow
*Assistant Examiner* — Melissa Hoban
(74) *Attorney, Agent, or Firm* — Schwegman Lundberg & Woessner, P.A.

(57) ABSTRACT

An implant configured for fusing a first bone segment and a second bone segment during an operative procedure and constructed in accordance to one example of the present disclosure includes an implant body, a first bone interfacing portion and a second bone interfacing portion. The implant body can extend longitudinally between an insertion end and an opposite end. The first bone interfacing portion can be provided on the implant body and be configured to be implanted relative to the first bone segment. The second bone interfacing portion can be provided on the implant body and be configured to be implanted relative to the second bone segment. The first and second bone interfacing portions can be inserted dorsally into the first and second bone segments, respectively.

19 Claims, 8 Drawing Sheets

(52) U.S. Cl.
CPC ................ *A61B 2017/0647* (2013.01); *A61F 2002/4233* (2013.01)

(56) References Cited

U.S. PATENT DOCUMENTS

| | | | | |
|---|---|---|---|---|
| 6,342,076 | B1* | 1/2002 | Lundborg | A61F 2/30742 623/21.11 |
| 6,533,454 | B1* | 3/2003 | Kaikkonen | A61B 17/92 378/205 |
| 7,041,106 | B1 | 5/2006 | Carver et al. | |
| 7,291,175 | B1* | 11/2007 | Gordon | A61F 2/4225 606/98 |
| 2003/0040750 | A1* | 2/2003 | Stoffella | A61B 17/68 606/324 |
| 2003/0139746 | A1 | 7/2003 | Groiso | |
| 2004/0092937 | A1 | 5/2004 | Criscuolo et al. | |
| 2007/0093834 | A1* | 4/2007 | Stevens | A61B 17/0401 606/279 |
| 2008/0109018 | A1 | 5/2008 | Martin | |
| 2008/0167668 | A1* | 7/2008 | Criscuolo | A61B 17/122 606/151 |
| 2008/0294195 | A1* | 11/2008 | Egli | A61B 17/705 606/246 |
| 2009/0105767 | A1* | 4/2009 | Reiley | A61F 2/4202 606/301 |
| 2011/0093018 | A1* | 4/2011 | Prasad | A61B 17/1728 606/282 |
| 2013/0325076 | A1* | 12/2013 | Palmer | A61B 17/1739 606/318 |
| 2014/0018812 | A1* | 1/2014 | Graham | A61B 17/1739 606/87 |
| 2014/0194999 | A1* | 7/2014 | Orbay | A61B 17/8095 623/21.12 |
| 2015/0088136 | A1* | 3/2015 | Kotuljac | A61B 17/7291 606/64 |
| 2016/0015437 | A1* | 1/2016 | Elleby | A61B 17/7291 606/329 |

FOREIGN PATENT DOCUMENTS

| | | |
|---|---|---|
| EP | 1813825 A1 | 8/2007 |
| FR | 2844445 A1 | 3/2004 |
| WO | WO-2016160372 A2 | 10/2016 |

OTHER PUBLICATIONS

"International Application Serial No. PCT/US2016/023094, Invitation to Pay Add'l Fees and Partial Search Report Mailed Aug. 31, 2012", 7 pgs.

"International Application Serial No. PCT/US2016/023094, Written Opinion mailed Nov. 3, 2016", 9 pgs.

* cited by examiner

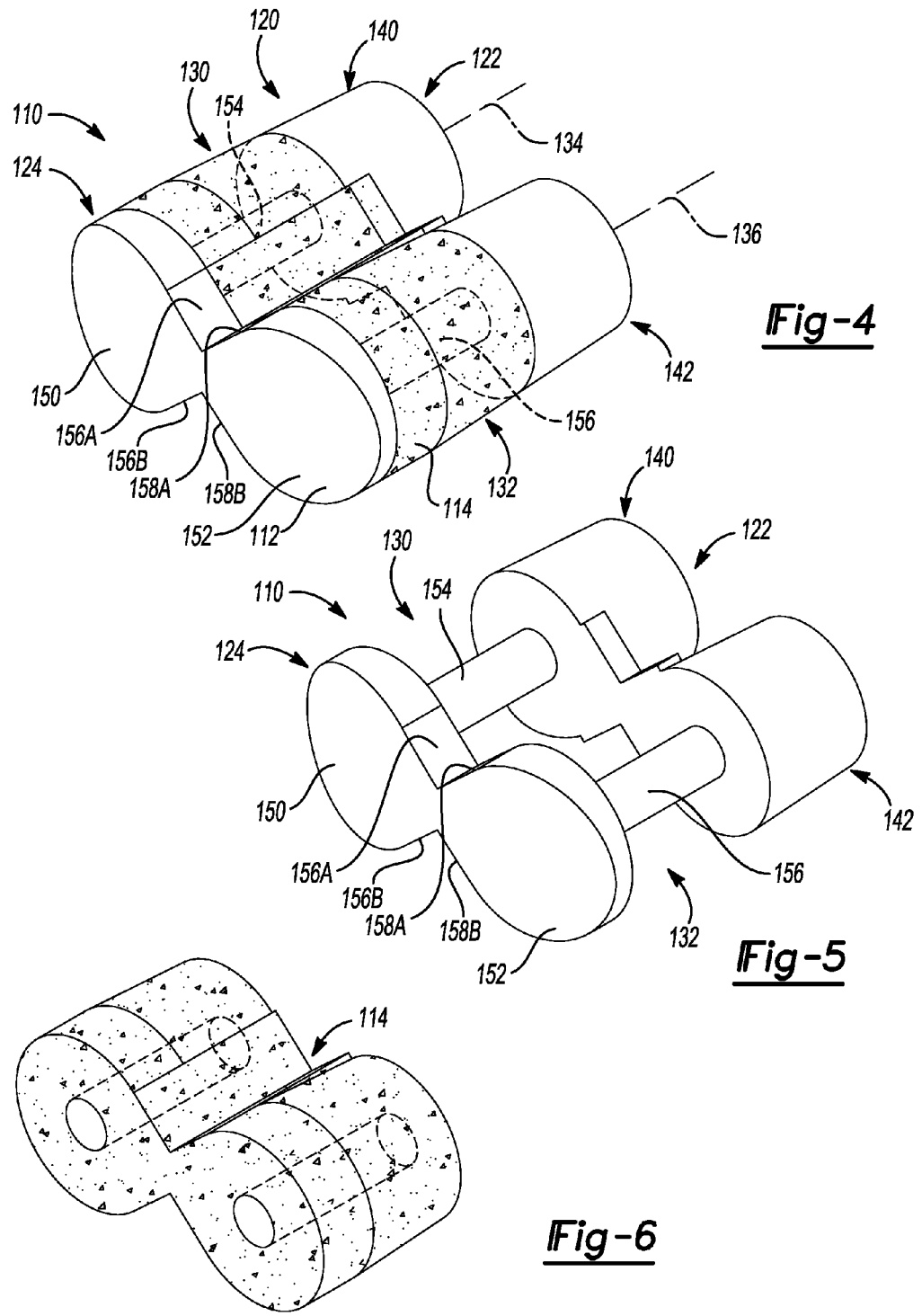

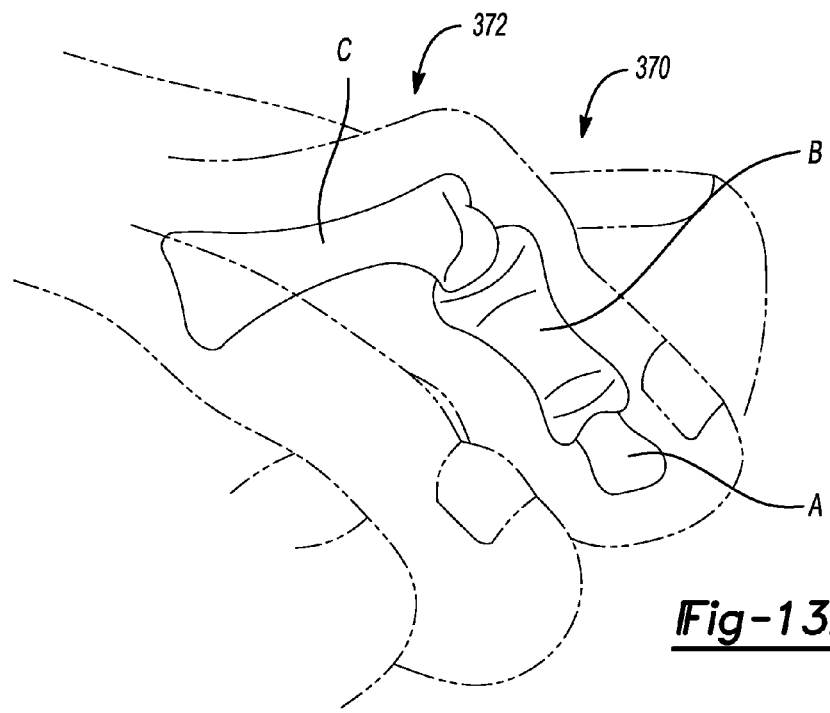
*Fig-13A*
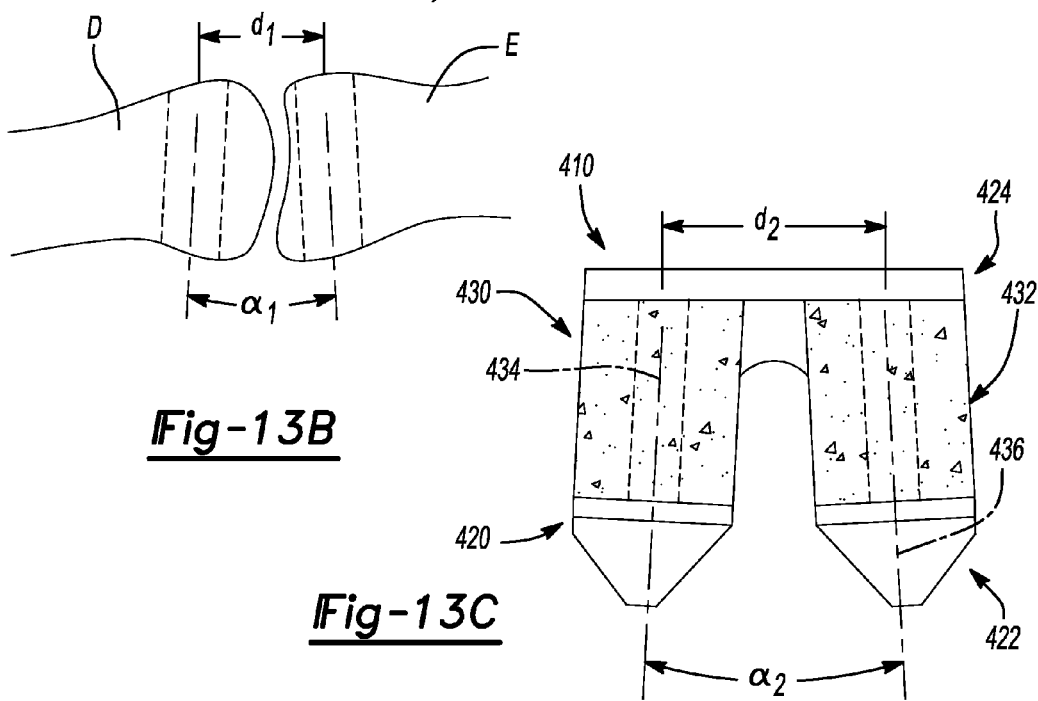
*Fig-13B*
*Fig-13C*

IMPLANT CONFIGURED FOR HAMMERTOE AND SMALL BONE FIXATION

FIELD

The present disclosure relates generally to bone fixation systems and, more particularly, to fixation devices and techniques for bone fusion to correct a hammertoe condition.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Deformities of the fingers and toes are common conditions encountered by orthopedists and podiatrists. Patients with digital deformities often experience significant pain from structural abnormalities. Some of these abnormalities are acquired, caused by traumatic injuries, neuromuscular pathologies, systemic diseases, or mechanical problems secondary to extrinsic pressures. The deformities are popularly known as either mallet finger, jersey finger, coach's finger, hammer toe, as well as a host of others indicative of several different pathologies.

Hammer toe is generally described in medical literature as an acquired disorder, typically characterized by hypertension of the metatarsophalangeal joint (MTPJ), hyperflexion of the proximal interphalangeal joint (PIPJ), and hypertension of the distal interphalangeal joint (DIPJ). Although this condition can be conservatively managed such as through the use of orthotic devices, in certain instances surgical intervention is required.

To ensure success of a surgical procedure, a proximal interphalangeal (PIP) joint arthrodesis is typically performed. Newer implants sued in hammertoe procedures fuse only the hammertoe joint but require the surgeon to distract the DIPJ in order to extend over the distal end of the implant after the first half of the implant has been inserted into PIPJ. It can be difficult to perform such steps in a minimally invasive fashion. In this regard, the distraction can cause issues with nerves and blood supply to the distal end of the toe.

SUMMARY

This section provides a general summary of the disclosure, and is not a comprehensive disclosure of its full scope or all of its features.

An implant configured for fusing a first bone segment and a second bone segment during an operative procedure and constructed in accordance to one example of the present disclosure includes an implant body, a first bone interfacing portion and a second bone interfacing portion. The implant body can extend longitudinally between an insertion end and an opposite end. The first bone interfacing portion can be provided on the implant body and be configured to be implanted relative to the first bone segment. The second bone interfacing portion can be provided on the implant body and be configured to be implanted relative to the second bone segment. The first and second bone interfacing portions can be inserted dorsally into the first and second bone segments, respectively.

According to additional features, the first bone interfacing portion can further comprise a first insertion portion that generally tapers toward the insertion end. The first insertion portion can be conical. The second bone interfacing portion can further comprise a second insertion portion that generally tapers toward the insertion end. The second bone interfacing portion can be conical.

According to other features, the first bone interfacing portion can further comprise first and second engagement portions formed at the opposite end. The first insertion and engagement portions can be offset by a first connecting shaft. The second insertion and engagement portions can be offset by a second connecting shaft. The first engaging portion can extend along a first bone engaging axis. The second bone engaging portion can extend along a second bone engaging axis. In one configuration, the first and second axes can be parallel. In another configuration, the first and second axes can converge toward the insertion end. In another configuration, the first and second axes can diverge toward the insertion end.

According to still other features, the implant can further comprise a porous metal portion disposed between (i) the first insertion portion and the first engagement portion and (ii) the second insertion portion and the second engagement portion. The implant body can further comprise a wedge disposed between the first and second bone interfacing portions. The wedge can generally extend between and taper from the opposite end to the insertion end. The wedge can include (i) a first bone engaging face configured to engage the first bone segment and (ii) a second engaging face configured to engage the second bone segment. The first and second bone engaging faces can extend along converging planes. The first and second engagement portions can comprise a geometry that defines two intersecting circles.

An implant configured for fusing a first bone segment and a second adjacent bone segment during an operative procedure according to another example of the present disclosure includes an implant body, a first bone interfacing portion, a second bone interfacing portion and a wedge. The implant body can have a solid metal portion and a porous metal portion. The implant body can extend longitudinally between an insertion end and an opposite end. The first bone interfacing portion can be provided on the implant body and have a first tapered end. The first bone interfacing portion can be configured to be implanted relative to the first bone segment. The second bone interfacing portion can be provided on the implant body and have a second tapered end. The second bone interfacing portion can be configured to be implanted relative to the second bone segment. The wedge can be configured on the implant body between the first and second bone interfacing portions. The wedge can generally extend between and taper from the opposite end to the insertion end. The first and second bone interfacing portions can be inserted dorsally into the first and second bone segments, respectively.

According to other features, the wedge can include (i) a first bone engaging face configured to engage the first bone segment and (ii) a second bone engaging face configured to engage the second bone segment. The first and second bone engaging faces can extend along converging planes. The first and second engagement portions comprise a geometry that defines two intersecting circles. The first and second engagement portions can extend along longitudinal axes that converge. In another example, the first and second engagement portions can extend along longitudinal axes that diverge.

A method of inserting an implant into a first bone segment and a second adjacent bone segment to fuse the first bone segment to the second bone segment is provided. An implant body is provided having a first and a second bone interfacing portion that extend longitudinally between an insertion end and an opposite end. A first bone hole is prepared generally inferiorly into the first bone segment. A second bone hole is prepared generally inferiorly into the second bone segment. The first and second bone interfacing portions are inserted dorsally into the respective first and second bone holes thereby fusing the first and second bone segments together.

According to additional features of the method, a first conically shaped insertion portion formed on the first bone interfacing portion is located into the first bone hole. A second conically shaped insertion portion formed on the second bone interfacing portion is located into the second bone hole. The first and second bone interfacing portions are concurrently advanced into the respective first and second bone holes. The implant can further comprise a wedge generally extending between the first and second bone interfacing portions. The wedge can include (i) a first bone engaging face configured to engage the first bone segment and (ii) a second bone engaging face configured to engage the second bone segment. The first and second bone engaging faces can extend along converging planes. The first bone engaging face can be slidably advanced along the first bone segment concurrently to the second bone engaging face slidably advancing along the second bone segment.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 4 is a perspective view of an implant configured for fusing a first phalange and a second adjacent phalange and constructed in accordance with another example of the present disclosure;

FIG. 5 is a perspective view of a solid metal portion of the implant of FIG. 4;

FIG. 6 is a perspective view of a porous metal portion of the implant of FIG. 4;

FIG. 13A is a partial lateral perspective view of a right human foot about to undergo a PIPJ arthrodesis procedure on the long toe in accordance with one example of the present disclosure;

FIG. 13B is a lateral view of two bone segments;

FIG. 13C is a side view of another exemplary implant having bone interfacing portions that diverge;

DETAILED DESCRIPTION

The following description is merely exemplary in nature and is not intended to limit the present disclosure, its application, or uses. Examples are provided so that this disclosure will be thorough, and will fully convey the scope to those who are skilled in the art. Numerous specific details are set forth such as examples of specific components, devices, systems and/or methods, to provide a thorough understanding of the present disclosure. It will be apparent to those skilled in the art that specific details need not be employed, that examples shown herein may be embodied in many different forms and that neither should be construed to limit the scope of the disclosure.

The present teachings and related discussion is directed primarily to the treatment of a hammertoe condition, it is equally applicable to any situation where a first phalange and a second adjacent phalange, of either a toe or a finger, are to be joined or fused together. It will further be appreciated that while the following discussion is directed toward treatment of a hammertoe condition, the following implants may be additionally used in other bones. In this regard, the following disclosure is not limited to implants used in phalanges. In other examples, the following implants may be used on any adjacent bones or on a fractured bone. As used herein the term "bone segment" is used to refer to a bone or a bone portion resulting from a fracture.

Figure 1:
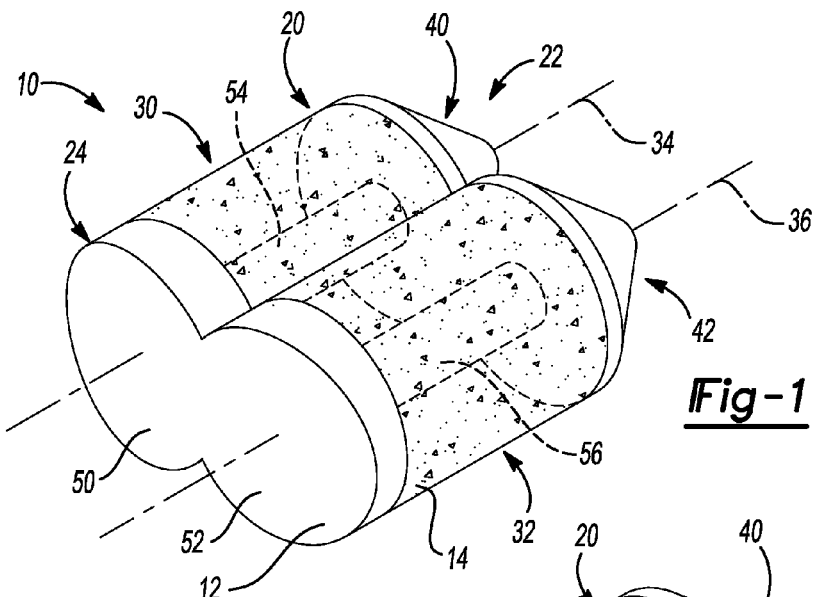
FIG. 1 is a perspective view of an implant configured for fusing a first phalange and a second adjacent phalange and constructed in accordance to one example of the present disclosure.
Figure 2:
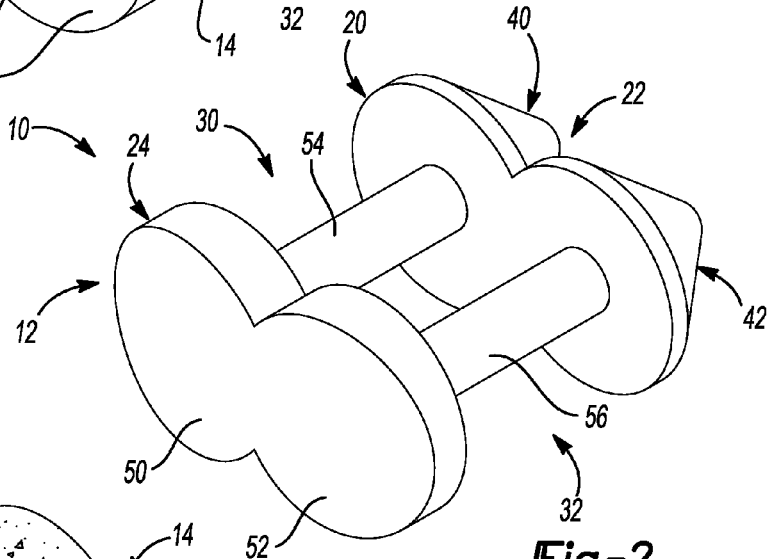
FIG. 2 is a perspective view of a solid metal portion of the implant of FIG. 1.
Figure 3:
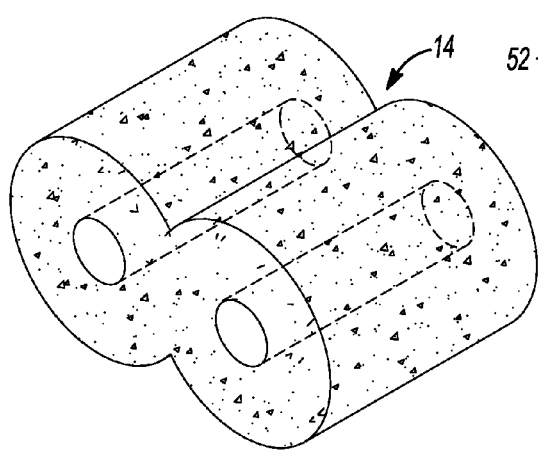
FIG. 3 is a perspective view of a porous metal portion of the implant of FIG. 1.

With initial reference to FIGS. 1-3, an exemplary implant configured for fusing a first phalange and a second adjacent phalange during an operative procedure is shown and generally identified at reference numeral 10. The implant 10 can be formed of a biocompatible alloy, such as a titanium alloy. In one exemplary implementation, the implant 10 can be formed using an additive manufacturing process with a titanium alloy core 12 (FIG. 2) and a porous metal titanium alloy structure 14 (FIG. 3).

In one exemplary implementation, the porous metal structure 14 can be a formed from a titanium alloy using an additive manufacturing process, such as with OsseoTi™, which is commercially available from Biomet Manufacturing, LLC (Warsaw, Ind., USA), Briefly, however, OsseoTi™ is highly biocompatible, has high corrosion resistance and includes a highly interconnected porous architecture that mimics the porous structure of human cancellous bone, which can enhance bone integration and in-growth. In one exemplary implementation, OsseoTi™ can include a porous construct with a porosity of 70%.

The implant 10 includes an implant body 20 that extends longitudinally between an insertion end 22 and an opposite end 24. The implant body 20 further includes a first bone interfacing portion 30 and a second bone interfacing portion 32. The first bone interfacing portion 30 extends along a first bone engaging axis 34 and is configured to be implanted relative to a first phalange. The second bone interfacing portion 32 extends along a second bone engaging axis 36 and is configured to be implanted relative to a second phalange. In the example shown in FIGS. 1-3 the first and second axes 34 and 36 are parallel to each other. As will be described herein, the first and second bone interfacing portions 30 and 32 are configured to be inserted dorsally along the respective first and second bone engaging axes 34 and 36 and into the first and second phalanges, respectively.

The first bone interfacing portion 30 can include a first insertion portion 40. The first insertion portion 40 can generally be in the geometry of a cone having a conical profile that tapers toward the insertion end 20. Similarly, the second bone interfacing portion 32 can include a second insertion portion 42. The second insertion portion 42 can generally be in the geometry of a cone having a conical profile that tapers toward the insertion end 20.

The first bone interfacing portion 30 further includes a first engagement portion 50 formed at an opposite end of the first insertion portion 40. The second bone interfacing portion 32 further includes a second engagement portion 52 formed at an opposite end of the second insertion portion 42. The first engagement portion 50 and the first insertion portion 40 can be connected and offset relative to each other by a first connecting shaft 54. Similarly, the second engagement portion 52 and the second insertion portion 42 can be connected and offset relative to each other by a second connecting shaft 56. In one configuration, the first and second engagement portions 50 and 52 can provide a surface for engaging during advancing the implant 10 into the respective first and second phalanges. In the example shown, the first and second engagement portions 50 and 52 have a geometry that defines two intersecting circles. Other configurations are contemplated. As shown in FIGS. 1-3, the porous metal structure 14 is generally disposed on the core 12 between the first and second insertion portions 40, 42 and the first and second engagement portions 50, 52. In particular, the first and second insertion portions 40 and 42 can be formed of solid core 12 to assist in insertion of the implant 10 into the respective first and second phalanges.

With reference now to FIGS. 4-6, an implant configured for fusing a first phalange and a second adjacent phalange during an operative procedure and constructed in accordance to another example is shown and generally identified at reference numeral 110. The implant 110 can be formed of a biocompatible alloy, such as a titanium alloy. The implant 110 can be formed using an additive manufacturing process identified above with a titanium core 112 (FIG. 5) and a porous metal titanium alloy structure 114 (FIG. 6). The porous metal alloy structure 114 may be formed of OsseoTi described above.

The implant 110 can include an implant body 120 that extends longitudinally between an insertion end 122 and an opposite end 124. The implant body 120 further includes a first bone interfacing portion 130 and a second bone interfacing portion 132. The first bone interfacing portion 130 extends along a first bone engaging axis 134 and is configured to be implanted relative to a first phalange. The second bone interfacing portion 132 extends along a second bone engaging axis 136 and is configured to be implanted relative to a second phalange. In the example shown in FIGS. 4-6, the first and second axes 134 and 136 are parallel to each other. As will be described herein, the first and second bone interfacing portions 130 and 132 are configured to be inserted dorsally, similar to the other examples disclosed herein, along the respective first and second bone engaging axes 134 and 136 and into the first and second phalanges, respectively.

The first bone interfacing portion 130 can include a first insertion portion 140. The first insertion portion 140 can taper toward the insertion end 120. In another example, the first insertion portion 140 can have a conical profile similar to shown in FIGS. 1-3. Similarly, the second bone interfacing portion 132 can include a second insertion portion 142. The second insertion portion 142 can also taper toward the insertion end 122 and/or have a conical profile similar to shown in FIGS. 1-3. Regardless, the outer surface of the first and second insertion portions 140 and 142 are configured to facilitate easy insertion into a prepared bone hole as will become appreciated herein.

The first bone interfacing portion 130 further includes a first engagement portion 150 formed at an opposite end of the first insertion portion 140. The second bone interfacing portion 132 further includes a second engagement portion 152 formed at an opposite end of the second insertion portion 142. The first engagement portion 150 and the first insertion portion 140 can be connected and offset relative to each other by a first connecting shaft 154.

Similarly, the second engagement portion 152 and the second insertion portion 142 can be connected and offset relative to each other by a second connecting shaft 156. In one configuration, the first and second engagement portions 150 and 152 can provide a surface for engaging during advancing the implant 110 into the respective first and second phalanges. In the example shown, the first and second engagement portions 150 and 152 have a geometry that generally defines two converging teardrops. In this regard, the first engagement portion 150 has a first pair of generally planar surfaces 156A, 156B and the second engagement portion 152 has a second pair of generally planar surfaces 158A and 158B. The corresponding first and second planar surfaces 156A and 158A intersect and the first and second planar surface 156B and 158B intersect.

As will be explained in greater detail herein, the first and second pairs of planar surfaces 156A, 156B and 158A, 158B can correspond to cuts made in the respective adjacent phalanges to accommodate the implant 110. Other configurations are contemplated. As shown in FIGS. 4-6, the porous metal structure 114 is generally disposed on the core 112 between the first and second insertion portions 140, 142 and the first and second engagement portions 150, 152. In particular, the first and second insertion portions 140 and 142 can be formed of solid core 112 to assist in insertion of the implant 110 into the respective first and second phalanges.

Figure 7:
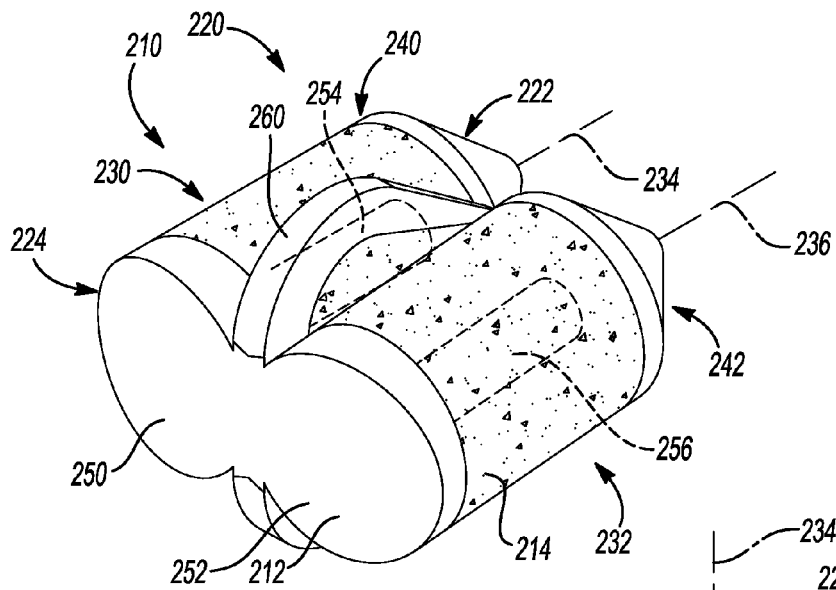
FIG. 7 is a perspective view of an implant configured for fusing a first phalange and a second adjacent phalange and constructed in accordance with yet another example of the present disclosure.
Figure 8:
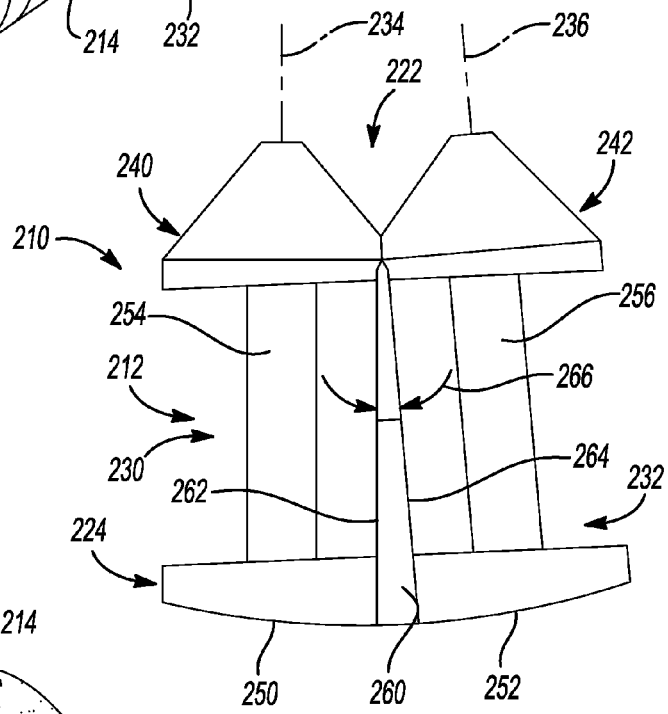
FIG. 8 is a perspective view of a solid metal portion of the implant of FIG. 7.
Figure 9:
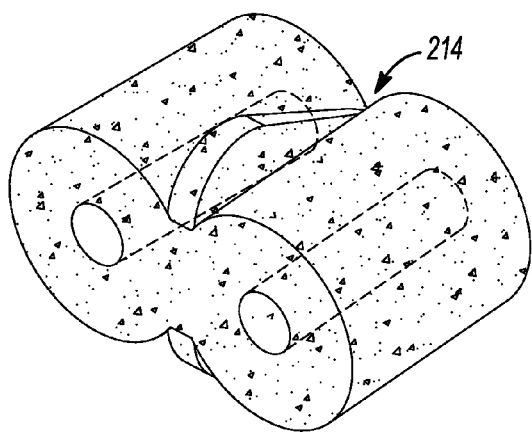
FIG. 9 is a perspective view of a porous metal portion of the implant of FIG. 7.

With reference now to FIGS. 7-9, an implant configured for fusing a first phalange and a second adjacent phalange during an operative procedure and constructed in accordance to another example is shown and generally identified at reference numeral 210. The implant 210 can be formed of a biocompatible alloy, such as a titanium alloy. The implant 210 can be formed using an additive manufacturing process identified above with a titanium core 212 (FIG. 8) and a porous metal titanium alloy structure 214 (FIG. 9). The porous metal alloy structure 214 may be formed of OsseoTi described above.

The implant 210 can include an implant body 220 that extends longitudinally between an insertion end 222 and an opposite end 224. The implant body 220 further includes a first bone interfacing portion 230 and a second bone interfacing portion 232. The first bone interfacing portion 230 extends along a first bone engaging axis 234 and is configured to be implanted relative to a first phalange. The second bone interfacing portion 232 extends along a second bone engaging axis 236 and is configured to be implanted relative to a second phalange. As best illustrated in FIG. 8, the first and second axes 234 and 236 define converging axes. As will be described herein, the first and second bone interfacing portions 230 and 232 are configured to be inserted dorsally, similar to the other examples disclosed herein, along the respective first and second bone engaging axes 234 and 236 and into the first and second phalanges, respectively.

The first bone interfacing portion 230 can include a first insertion portion 240. The first insertion portion 240 can taper toward the insertion end 222. In the example shown, first insertion portion 240 has a conical profile similar to shown in FIGS. 1-3. Similarly, the second bone interfacing portion 232 can include a second insertion portion 242. The second insertion portion 242 can also taper toward the insertion end 222 and/or have a conical profile similar to shown in FIGS. 1-3. Regardless, the outer surface of the first and second insertion portions 240 and 242 are configured to facilitate easy insertion into a prepared bone hole as will become appreciated herein.

The first bone interfacing portion 230 further includes a first engagement portion 250 formed at an opposite end of the first insertion portion 240. The second bone interfacing portion 232 further includes a second engagement portion 252 formed at an opposite end of the second insertion portion 242. In the example shown in FIG. 18, the first and second engagement portions 250 and 252 can collectively have an arcuate outer profile. The first engagement portion 250 and the first insertion portion 240 can be connected and offset relative to each other by a first connecting shaft 254.

Similarly, the second engagement portion 252 and the second insertion portion 242 can be connected and offset relative to each other by a second connecting shaft 256. In one configuration, the first and second engagement portions 250 and 252 can provide a surface for engaging during advancing the implant 210 into the respective first and second phalanges. In the example shown, the first and second engagement portions 250 and 252 have a geometry that defines two disk shaped portions that converge into a central wedge 260. The wedge 260 includes first and second generally planar surfaces 262 and 264 (FIG. 8) that converge toward the insertion end 222. In one non-limiting example, the first and second planar surfaces 262 and 264 define an angle 266 of about 10 degrees. It will be appreciated that other angles may be provided. Moreover, it is contemplated that a kit of implants may be offered having a variety of geometries including various wedges 260 that may be selected intraoperatively according to a given patient's needs.

As will be explained in greater detail herein, the first and second planar surfaces 262 and 264 are configured to slidably engage respective phalanges during insertion of the implant 210 to further encourage the phalanges to obtain a desired orientation. As shown in FIGS. 7-9, the porous metal structure 214 is generally disposed on the core 212 between the first and second insertion portions 240, 242 and the first and second engagement portions 250, 252. In particular, the first and second insertion portions 240 and 242 can be formed of solid core 212 to assist in insertion of the implant 210 into the respective first and second phalanges.

Figure 10:
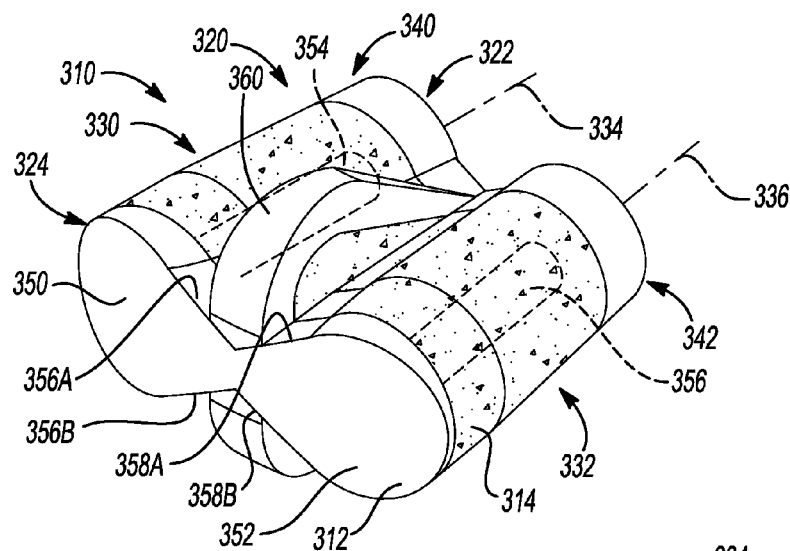
FIG. 10 is a perspective view of an implant configured for fusing a first phalange and a second adjacent phalange and constructed in accordance to another example of the present disclosure.
Figure 11:
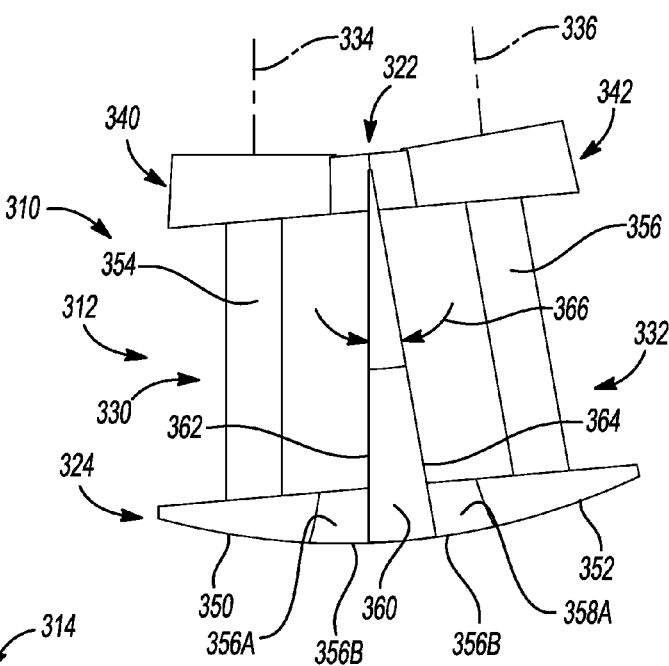
FIG. 11 is a perspective view of a solid metal portion of the implant of FIG. 10.
Figure 12:
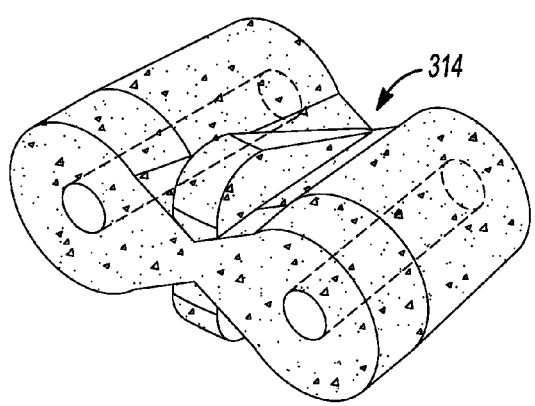
FIG. 12 is a perspective view of a porous metal portion of the implant of FIG. 10.

With reference now to FIGS. 10-12, an implant configured for fusing a first phalange and a second adjacent phalange during an operative procedure and constructed in accordance to another example is shown and generally identified at reference numeral 310. The implant 310 can be formed of a biocompatible alloy, such as a titanium alloy. The implant 310 can be formed using an additive manufacturing process identified above with a titanium core 312 (FIG. 11) and a porous metal titanium alloy structure 214 (FIG. 12). The porous metal alloy structure 314 may be formed of OsseoTi described above.

The implant 310 can include an implant body 320 that extends longitudinally between an insertion end 322 and an opposite end 324. The implant body 320 further includes a first bone interfacing portion 330 and a second bone interfacing portion 332. The first bone interfacing portion 330 extends along a first bone engaging axis 334 and is configured to be implanted relative to a first phalange. The second bone interfacing portion 332 extends along a second bone engaging axis 336 and is configured to be implanted relative to a second phalange. As best illustrated in FIG. 11 the first and second axes 334 and 336 define converging axes. As will be described herein, the first and second bone interfacing portions 330 and 332 are configured to be inserted dorsally, similar to the other examples disclosed herein, along the respective first and second bone engaging axes 334 and 336 and into the first and second phalanges, respectively.

The first bone interfacing portion 330 can include a first insertion portion 340. The first insertion portion 340 can taper toward the insertion end 322. In the example shown, first insertion portion 340 has a conical profile similar to shown in FIGS. 1-3. Similarly, the second bone interfacing portion 332 can include a second insertion portion 342. The second insertion portion 342 can also taper toward the insertion end 322 and/or have a conical profile similar to shown in FIGS. 1-3. Regardless, the outer surface of the first and second insertion portions 340 and 342 are configured to facilitate easy insertion into a prepared bone hole as will become appreciated herein.

The first bone interfacing portion 330 further includes a first engagement portion 350 formed at an opposite end of the first insertion portion 340. The second bone interfacing portion 332 further includes a second engagement portion 352 formed at an opposite end of the second insertion portion 342. In the example shown in FIG. 11, the first and second engagement portions 350 and 352 can collectively have an arcuate outer profile. The first engagement portion 350 and the first insertion portion 340 can be connected and offset relative to each other by a first connecting shaft 354.

Similarly, the second engagement portion 352 and the second insertion portion 342 can be connected and offset relative to each other by a second connecting shaft 356. In one configuration, the first and second engagement portions 350 and 352 can provide a surface for engaging during advancing the implant 310 into the respective first and second phalanges. In the example shown, the first and second engagement portions 350 and 352 have a geometry that defines two teardrops that converge into a central wedge 360. The first engagement portion 350 has a first pair of generally planar surfaces 356A, 356B and the second engagement portion 352 has a second pair of generally planar surfaces 358A and 358B. The corresponding first and second planar surfaces 356A and 358A intersect and the first and second planar surface 356B and 358E intersect.

The wedge 360 includes first and second generally planar surfaces 362 and 364 that converge toward the insertion end 322. In one non-limiting example, the first and second planar surfaces 362 and 364 define an angle 366 of about 10 degrees. It will be appreciated that other angles may be provided. Moreover, it is contemplated that a kit of implants may be offered having a variety of geometries including various wedges 360 that may be selected intraoperatively according to a given patient's needs.

As will be explained in greater detail herein, the first and second planar surfaces 362 and 364 are configured to slidably engage respective phalanges during insertion of the implant 310 to further encourage the phalanges to obtain a desired orientation. As shown in FIGS. 10-12, the porous metal structure 314 is generally disposed on the core 312 between the first and second insertion portions 340, 342 and the first and second engagement portions 350, 352. In particular, the first and second insertion portions 340 and 342 can be formed of solid core 312 to assist in insertion of the implant 310 into the respective first and second phalanges.

Turning now to FIGS. 13A-14C, an exemplary PIPJ arthrodesis procedure using the implant 10 will be described. A partial lateral perspective view of a right human foot 370 about to undergo a PIPJ arthrodesis procedure on a long toe 372 is illustrated (FIG. 13A). The long toe 372 generally includes a distal phalange A, a proximal phalange B and a first metatarsal C. The example shown and described herein is directed toward fusion of the proximal phalange B and the first metatarsal C of the long toe 372. It will be appreciated however that the same may be applied to other adjacent bones in the toe or hand. FIG. 13B illustrates adjacent bone segments E and F. A distance d1 and a joint flexion angle $\alpha_1$ are defined between the phalanges E and F. FIG. 13C illustrates an implant 410 that includes an implant body 420 that extends longitudinally between an insertion end 422 and an opposite end 424. The implant body 420 further includes a first bone interfacing portion 430 and a second bone interfacing portion 432. The first bone interfacing portion 430 extends along a first bone engaging axis 434 and is configured to be implanted relative to a first phalange. The second bone interfacing portion 432 extends along a second bone engaging axis 436 and is configured to be implanted relative to a second phalange. The first and second axes 434 and 436 are diverging and define an angle $\alpha_2$. A distance d2 is defined between the first and second axes 434 and 436 at the opposite end 424. The first and second bone interfacing portions 430 and 432 are configured to be inserted dorsally, similar to the other examples disclosed herein, along the respective first and second bone engaging axes 434 and 436 and into the first and second phalanges, respectively. As will become appreciated herein, a distance or proximity of the phalanges E and F can be controlled by d1 and d2. Similarly, a joint flexion angle can be controlled by angles $\alpha_1$ and $\alpha_2$.

Figure 14A:
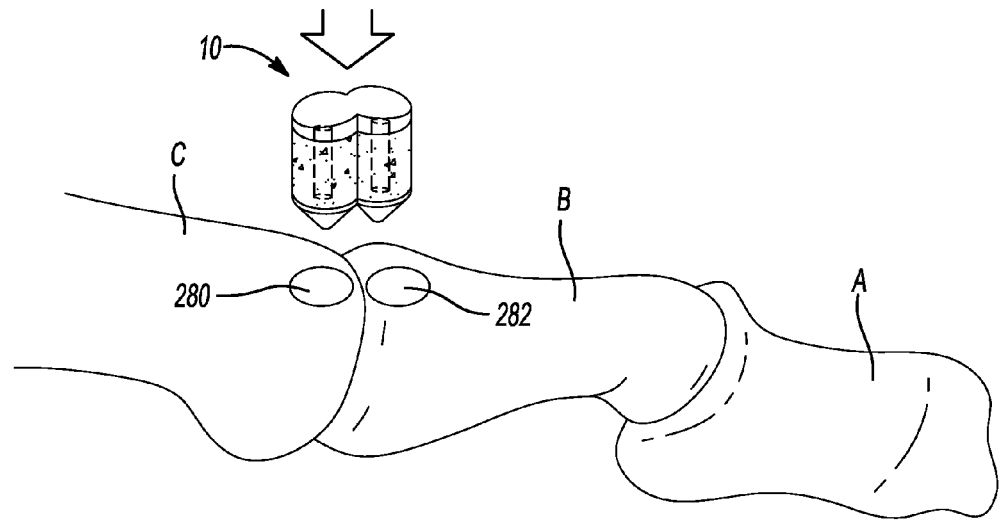
FIG. 14A is a lateral view of a long toe of the right foot shown in FIG. 13A including a distal phalange, proximal phalange and first metatarsal shown with a bone hole prepared into both of the proximal phalange and the first metatarsal for receipt of the implant shown in FIG. 1.
Figure 14B:
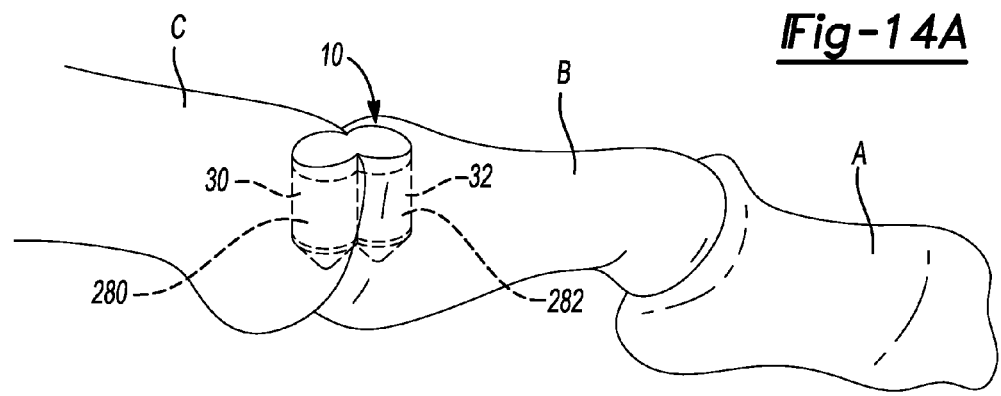
FIG. 14B is a lateral view of the long toe showing the implant of FIG. 1 implanted distally into the prepared bone holes in the proximal phalange and first metatarsal shown in FIG. 14A.
Figure 14C:
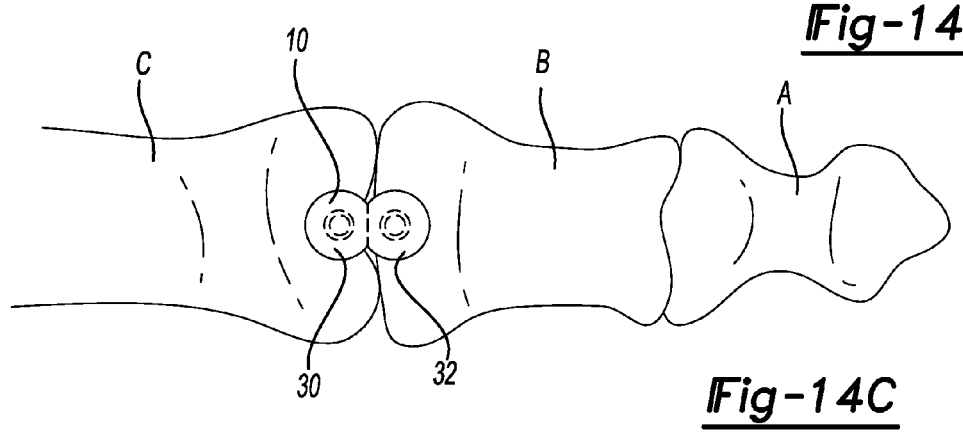
FIG. 14C is a superior view of the long toe and implant shown in 14B.

FIGS. 14A and 14B illustrate an exemplary sequence of implanting the implant 10 dorsally into a first bone hole 280 prepared in the proximal phalange A and a second bone hole 282 prepared in the first metatarsal C according to one example of the present disclosure. In one surgical method, minimal surrounding tissue of the proximal phalange B and the first metatarsal C at the PIPJ is removed. Because the implant 10 is implanted dorsally, only minimal amounts of tissue need to be disrupted as compared to a prior art implant that require significant manipulation of the proximal phalange B and the first metatarsal C to gain access to the IM canals of the proximal phalange B and the first metatarsal C.

Once the proximal phalange B and the first metatarsal C are oriented in a preferred (generally linear) orientation, bone holes 280 and 282 may be drilled into the respective proximal phalange B and the first metatarsal C (see FIG. 14A). The bone holes 280 and 282 can be generally parallel to match the axes 34 and 36 (FIG. 1). Next, the surgeon locates the first and second insertion portions 40 and 42 (see FIG. 1) onto the bone holes 280 and 282 and advances the first and second bone interfacing portions 30 and 32 of the implant 10 dorsally into the bone bones 280 and 282. In the implanted position, the proximal phalange B and the first metatarsal C are fused and the hammertoe deformation is corrected.

Figure 15A:
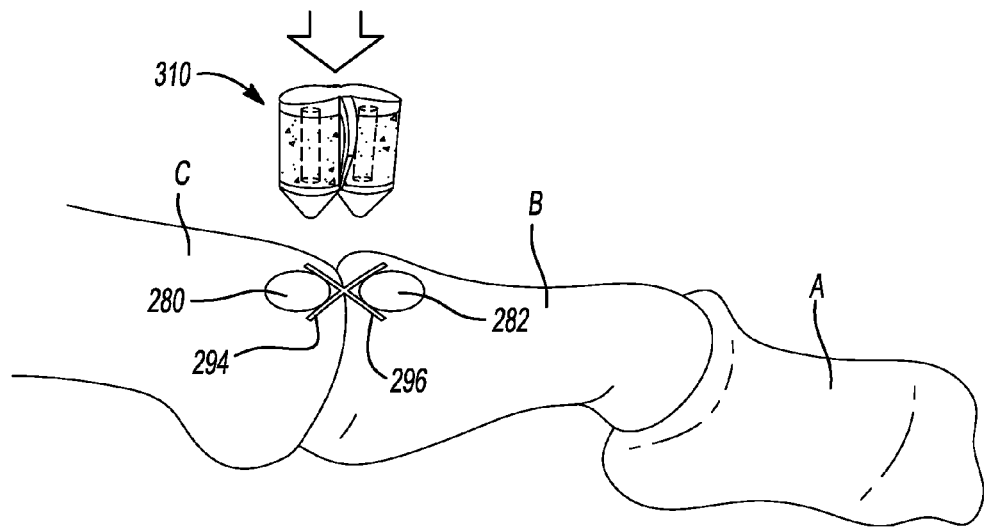
FIG. 15A is a lateral view of a long toe of the right foot shown in FIG. 13A including a distal phalange, proximal phalange and first metatarsal shown with a bone hole prepared into both of the proximal phalange and the first metatarsal for receipt of the implant shown in FIG. 10.
Figure 15B:
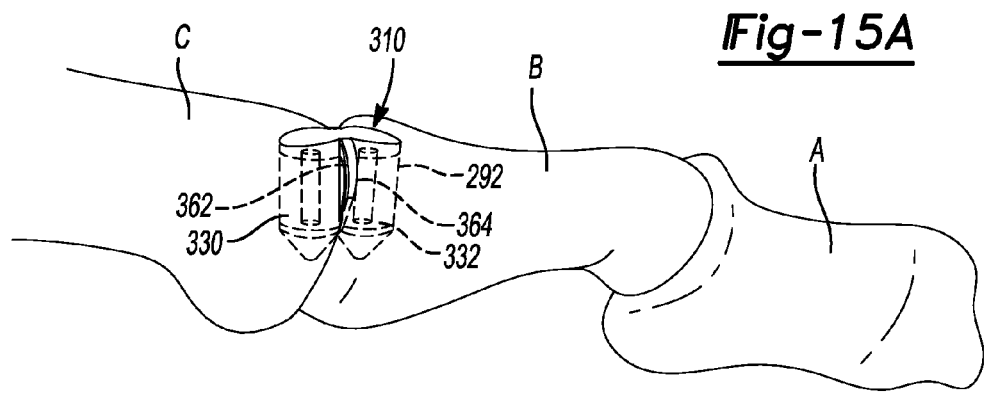
FIG. 15B is a lateral view of the long toe showing the implant of FIG. 10 implanted distally into the prepared bone holes in the proximal phalange and first metatarsal shown in FIG. 15A.
Figure 15C:
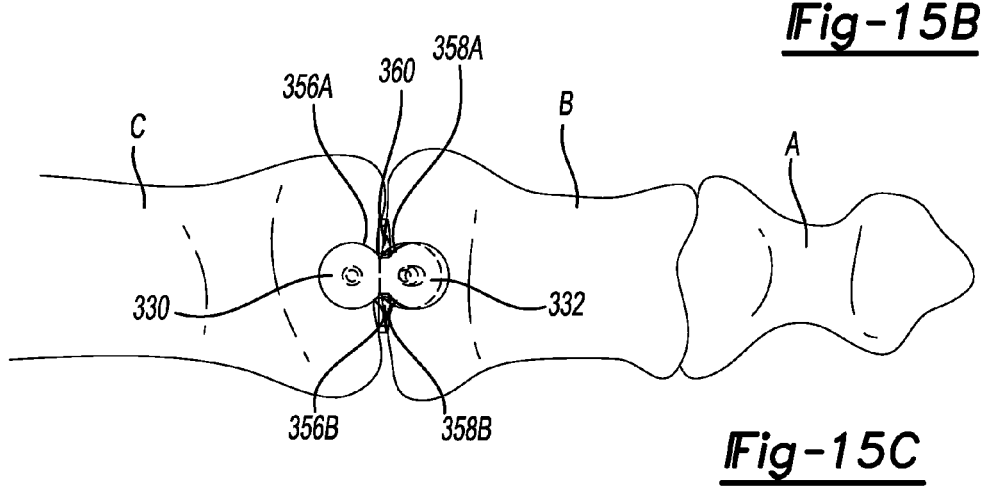
FIG. 15C is a superior view of the long toe and implant shown in 15B.

FIGS. 15A-15C illustrate a similar surgical procedure using the implant 310. Once the proximal phalange B and the first metatarsal C are oriented in a preferred (generally linear) orientation, bone holes 290 and 292 may be drilled into the respective proximal phalange B and the first metatarsal C (see FIG. 15A). The bone holes 290 and 292 can be generally parallel, or similar to the angle 366 to generally match the axes 334 and 336 (FIG. 11). In some examples the surgeon may prepare planar cuts 294 and 296 onto the proximal phalange B and first metatarsal C to match the profile of the planar surfaces 356A, 356B and 358A, 358C.

Next, the surgeon locates the first and second insertion portions 340 and 342 onto the bone holes 290 and 292 and advances the first and second bone interfacing portions 330 and 332 of the implant 310 dorsally into the bone bones 390 and 392. Notably, during the dorsal advancement, the planar surfaces 362 and 364 of the wedge 360 can slidably negotiate along the respective proximal phalange B and the first metatarsal C to further encourage proper alignment of the bone. In the implanted position, the proximal phalange B and the first metatarsal C are fused and the hammertoe deformation is corrected.

Figure 16:
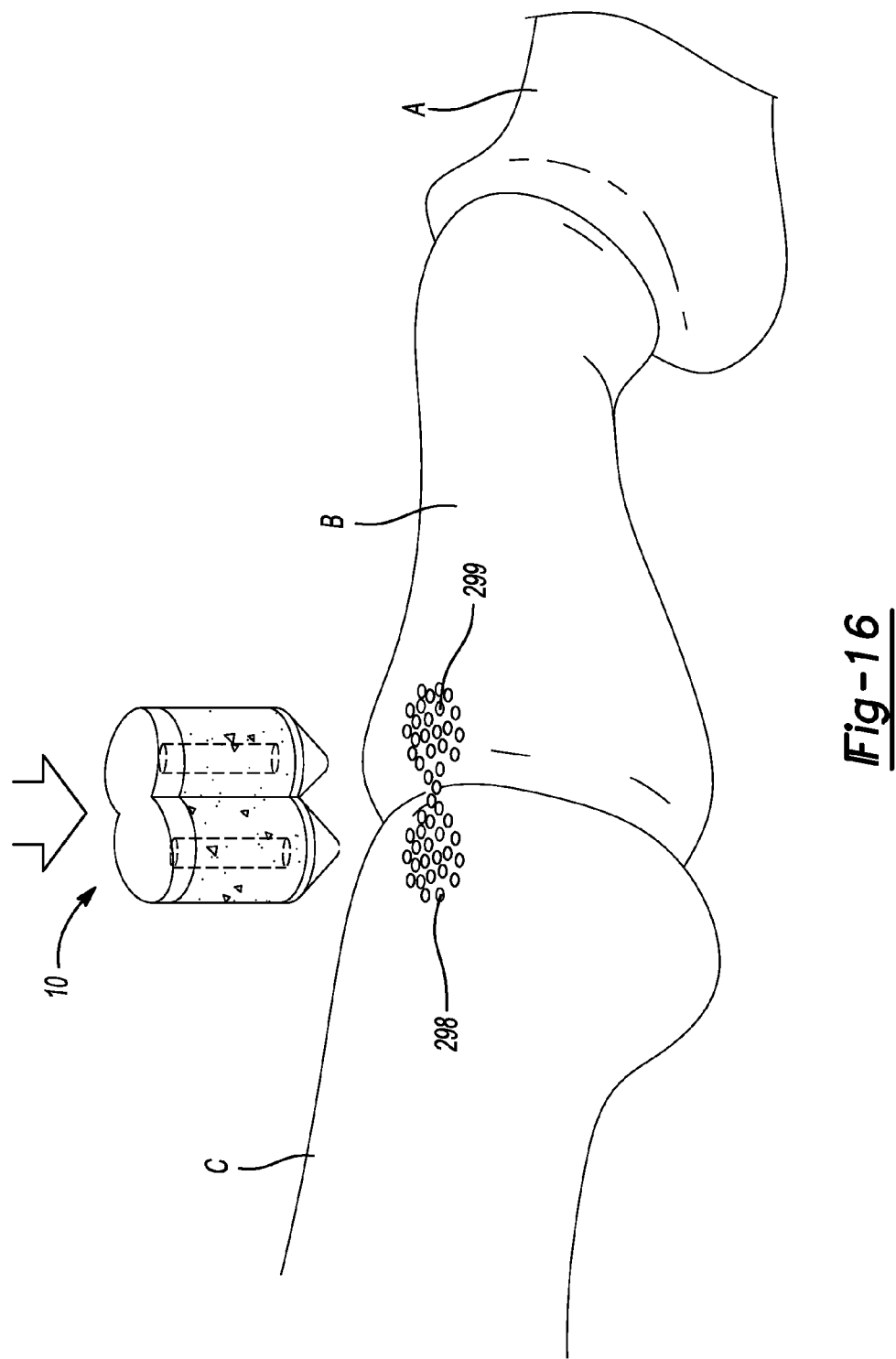
FIG. 16 is a lateral view of a long toe of the right foot shown in FIG. 13A including a distal phalange, proximal phalange and first metatarsal shown with a series of first bone holes prepared into the proximal phalange and a series of second bone holes prepared into the first metatarsal for receipt of an implant disclosed herein.

Turning now to FIG. 16, another surgical procedure according to the present disclosure will be described. In the previous examples, a single hole is described as being prepared into each phalange. In FIG. 16, a series of first holes 298 are prepared into the first metatarsal C. A series of second holes 299 are prepared into the proximal phalange B. As can be appreciated, several smaller diameter holes 298 and 299 may be prepared into the first metatarsal C and the proximal phalange B, respectively, to make up the larger overall shape of the desired implant.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An implant configured for fusing a first, bone segment and a second adjacent bone segment during an operative procedure, the implant comprising:
   an implant core that extends along an implant axis between an insertion end and an opposite end, the implant core comprising:
      a first core portion comprising a first insertion portion disposed on a first end of a first connecting shaft and a first engagement portion disposed on a second end of the first connecting shaft, the first connecting shaft having a major cross-sectional dimension that is less than a major cross-sectional dimension of the first insertion portion and a major cross-sectional dimension of the first engagement portion; and
      a second core portion comprising a second insertion portion disposed on a first end of a second connecting shaft and a second engagement portion disposed on a second end of the second connecting shaft, the second connecting shaft having a major cross-sectional dimension that is less than a major cross-sectional dimension of the second insertion portion and a major cross-sectional dimension of the second engagement portion; and
   a porous metal body matingly engaged with the implant core and extending along the implant axis between the first and second insertion portions and the first and second engagement portions of the implant core respectively;
   wherein the implant core and the porous metal body cooperatively define a first bone engaging portion dorsally insertable in a bore disposed in the first bone segment and a second bone engaging portion dorsally insertable in a bore disposed in the second bone segment; and
   wherein the first core portion and the second core portion are coupled such that, in cross-section, the first insertion portion and the second insertion portion define a pair of intersecting shapes.

2. The implant of claim 1, wherein the first insertion portion tapers toward the insertion end of the implant core.

3. The implant of claim 2, wherein the first insertion portion is conical.

4. The implant of claim 1, wherein the second insertion portion tapers toward the insertion end of the implant core.

5. The implant of claim 4, wherein the second insertion portion is conical.

6. The implant of claim 1, wherein the first connecting shaft and the second connecting shaft are spaced laterally apart from each other with respect to the implant axis.

7. The implant of claim 1, wherein the first bone engaging portion extends along a first bone engaging axis and the second bone engaging portion extends along a second bone engaging axis.

8. The implant of claim 7, wherein the first and second bone engaging axes are parallel.

9. The implant of claim 7, wherein the first and second bone engaging axes converge towards the insertion end.

10. The implant of claim 7, wherein the first and second bone engaging axes diverge towards the insertion end.

11. The implant of claim 1, wherein the implant core further comprises a wedge disposed between the first and second bone engaging portions, the wedge extending between and tapering from the opposite end towards the insertion end.

12. The implant of claim 11, wherein the wedge includes a first bone engaging face configured to engage the first bone segment and a second bone engaging face configured to engage the second bone segment, wherein the first and second bone engaging faces extend along converging planes.

13. The implant of claim 1, wherein at least one of the first pair and the second pair of intersecting shapes comprise two intersecting circles.

14. The implant of claim 1, wherein the intersecting shapes comprise two intersecting teardrops or two intersecting ovals.

15. The implant of claim 1, wherein the implant core is solid.

16. The implant of claim 1, wherein the implant core comprises titanium or a titanium alloy.

17. The implant of claim 1, wherein the porous metal body comprises titanium or a titanium alloy.

18. The implant of claim 1, wherein the porous metal body has a porosity of about 70%.

19. An implant, comprising:
   an implant core that extends along an implant axis between an insertion end and an opposite end, the implant core comprising:
      an insertion portion comprising a first insertion portion and a second insertion portion; and
      an engagement portion spaced from the insertion portion along the implant axis, the engagement portion comprising a first engagement portion and a second engagement portion; and
   a porous metal body matingly engaged with the implant core and extending along the implant axis between the insertion portion and the engagement portion of the implant core;

wherein the implant core and the porous metal body cooperatively define a first bone engaging portion dorsally insertable in a bore disposed in the first bone segment and a second bone engaging portion insertable in a bore disposed in the second bone segment; and wherein the first engagement portion and the second engagement portion are coupled such that, in cross-section, the first engagement portion and the second engagement portion define a pair of intersecting shapes.

* * * * *

UNITED STATES PATENT AND TRADEMARK OFFICE
CERTIFICATE OF CORRECTION

PATENT NO.       : 9,763,800 B2
APPLICATION NO.  : 14/661250
DATED            : September 19, 2017
INVENTOR(S)      : Finley et al.

It is certified that error appears in the above-identified patent and that said Letters Patent is hereby corrected as shown below:

In the Claims

In Column 11, Line 37, in Claim 1, delete "first," and insert --first-- therefor Signed and Sealed this
Nineteenth Day of June, 2018

Andrei Iancu
*Director of the United States Patent and Trademark Office*